(12) United States Patent
Gonzales, Jr.

(10) Patent No.: US 6,974,467 B1
(45) Date of Patent: Dec. 13, 2005

(54) METHOD AND APPARATUS FOR MAKING A PRECISE SURGICAL INCISION

(76) Inventor: Antonio Gonzales, Jr., 3207 20th St., Lubbock, TX (US) 79410

( * ) Notice: Subject to any disclaimer, the term of this patent is extended or adjusted under 35 U.S.C. 154(b) by 621 days.

(21) Appl. No.: 10/287,376

(22) Filed: Nov. 4, 2002

(51) Int. Cl.[7] ............................................. A61B 17/32
(52) U.S. Cl. ..................................... 606/167; 606/185
(58) Field of Search ................................ 606/167, 170, 606/172, 181, 183, 185, 190; 600/583–845, 600/573

(56) References Cited

U.S. PATENT DOCUMENTS

| | | | |
|---|---|---|---|
| 4,182,337 A | 1/1980 | Nickson | |
| 4,291,690 A | 9/1981 | Jessen | |
| 4,331,138 A | 5/1982 | Jessen | |
| 4,760,847 A | 8/1988 | Vaillancourt | |
| 5,217,007 A * | 6/1993 | Ciaglia | 128/207.29 |
| 5,279,285 A | 1/1994 | Griggs | |
| 5,330,432 A * | 7/1994 | Yoon | 604/164.12 |
| 5,967,143 A | 10/1999 | Klappenberger | |
| 5,988,168 A | 11/1999 | Bair | |
| 6,048,354 A | 4/2000 | Lawrence | |
| 6,077,284 A | 6/2000 | Piraka | |
| 6,200,274 B1 | 3/2001 | McNeirney | |
| 6,346,115 B1 | 2/2002 | Lawrence | |
| 6,398,743 B1 * | 6/2002 | Halseth et al. | 600/585 |

* cited by examiner

Primary Examiner—(Jackie) Tan-Uyen T. Ho
(74) Attorney, Agent, or Firm—L. Bruce Terry

(57) ABSTRACT

A method of surgically accessing and making an incision in a selected part of a body includes inserting a needle into part of the body and withdrawing fluid from the body through the needle to determine if the needle is located in the selected part of the body. Once properly located, a blade is moved along the length of the needle, making an adjacent incision. A depth of the blade relative to the end of the needle is indicated to the user. A surgical apparatus includes a hollow needle, having a needle point and a needle wall that defines a needle tube. A blade having a cutting edge and a blade base adjacent to the cutting edge is located adjacent to the needle wall. A platform slidably engages the needle for sliding along the length of the needle and holding the blade base adjacent to the needle.

19 Claims, 4 Drawing Sheets

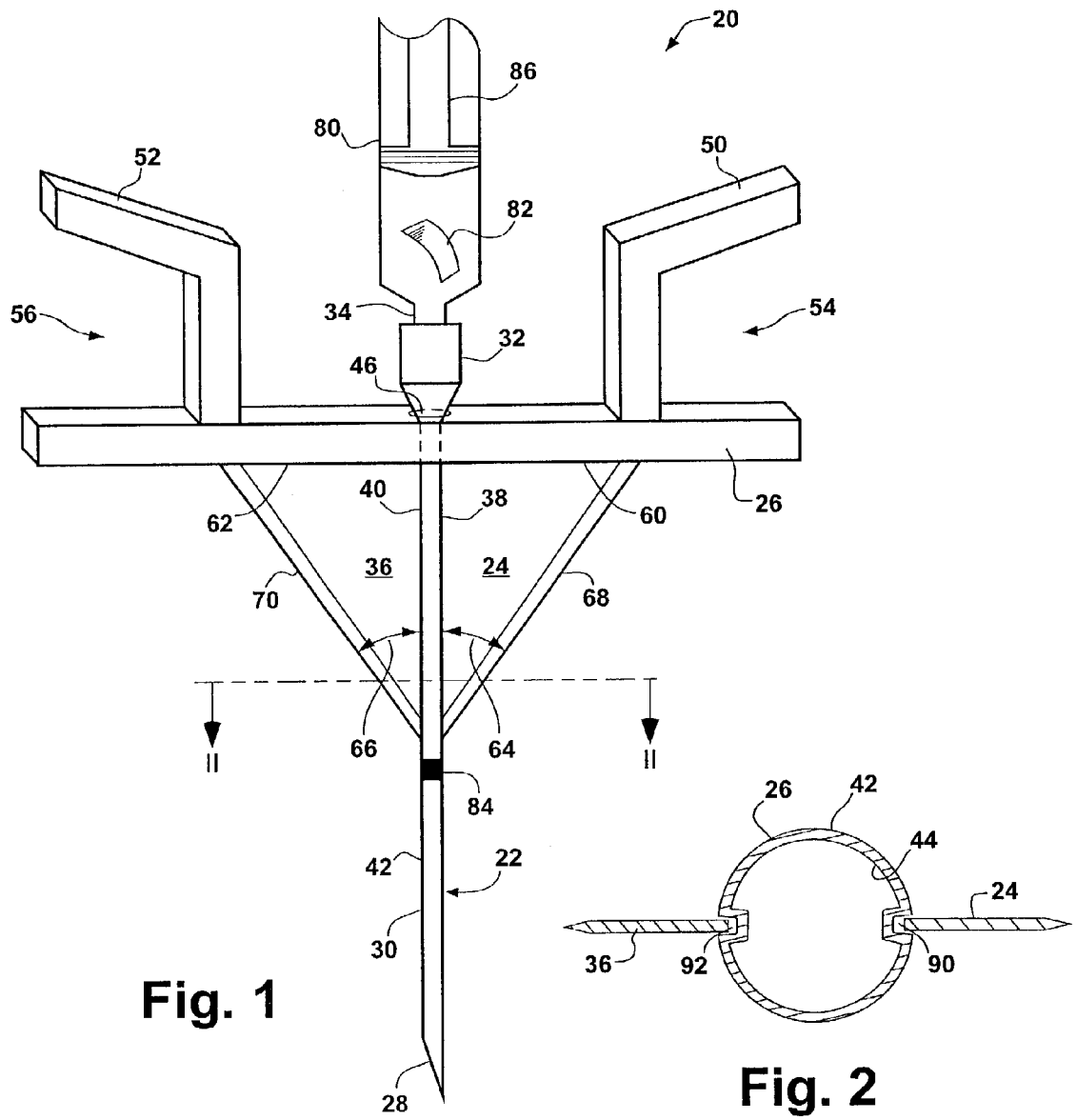
Fig. 1
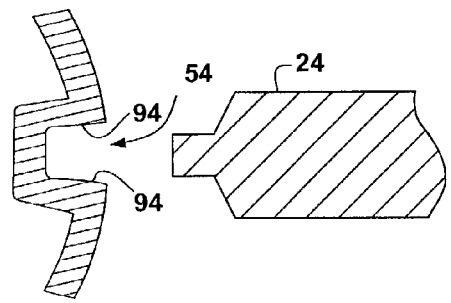
Fig. 2
Fig. 8

US 6,974,467 B1

METHOD AND APPARATUS FOR MAKING A PRECISE SURGICAL INCISION

BACKGROUND OF THE INVENTION

1. Field of the Invention

The present invention relates generally to surgical instruments and procedures, and more particularly to a method and apparatus for making a precise surgical incision.

2. Description of the Prior Art

In the medical treatment of a living being, whether human or animal, it is frequently necessary to make a precise surgical incision at a particular location, and at a particular depth, in the body. Such a precise incision may be needed for creating a working portal for arthroscopic surgery, endoscopic surgery or other surgical procedures that operate with cameras and tools on the end of a tube inserted into the body.

In another circumstance, a patient with a failed airway—where a patient is unable to oxygenate and ventilate, and the trachea is not in condition for intubation—may require a precise surgical incision for placing a breathing tube in the trachea. Such an incision is typically made in the neck of the patient's body by an emergency room medical practitioner, surgeon, or paramedic. Access to the trachea is typically gained by making an incision in the cricothyroid membrane in a procedure referred to as cricothyroidotomy, which is incision through skin and the cricothyroid membrane to secure a patient's airway for emergency relief of upper airway obstruction.

Precision is needed because an improperly located incision may result in accidental damage to vital organs, infection, misplacement of an endotracheal tube or other instrument, laceration of blood vessels, hemorrhaging, spread of diseases (e.g., AIDS and hepatitis), and the like. Safety of the operator making the incision is also a concern because the operator may be cut, which increases the operator's chance of acquiring a fatal disease such as AIDS and hepatitis.

In the prior art, U.S. Pat. No. 6,346,115 to Lawrence discloses a sliding knife and needle assembly for creating a percutaneous incision in a living body. The device has a hollow rectangular handle, with a solid needle extending therefrom. A knife blade is located inside the hollow handle and may be extended parallel to the axis of the needle for creating an incision for arthroscopic or endoscopic surgery. This device has the disadvantage of not supporting an analysis of fluid from the location of the tip of the needle. Further disadvantages include a structure wherein the needle is not in the plane of the blade, and an absence of an indication of the depth of the blade relative to the needle.

Therefore, there is a need for an improved method and apparatus for precisely locating a point of incision in a living body, wherein the improvements help a medical practitioner locate a point of incision prior to making an incision, and the depth of the incision relative to the located point is indicated to the practitioner.

SUMMARY OF THE INVENTION

A method of surgically accessing and making an incision in a selected part of a living body includes the steps of inserting a needle into part of the body and withdrawing fluid sample from the body through the needle to determine, by examining or testing the fluid, if the needle is located in the selected part of the body. Once the needle is properly located, the user slides a blade along the length of the needle to make an incision in the body adjacent to the needle. A depth of the blade relative to the end of the needle is indicated to the user.

According to one embodiment of the invention, a surgical apparatus for accessing and making an incision in a selected part of a living body includes a hollow needle, having a needle point and a needle wall that defines a needle tube. The needle is used for inserting into a selected part of the body and withdrawing a fluid sample. The apparatus has a blade having a cutting edge and a blade base adjacent to the cutting edge. The blade base is located adjacent to the needle wall along a portion of a length of the needle, and is used for making an incision in the body adjacent to the needle. A platform slidably engages the needle for sliding along the length of the needle and holding the blade base adjacent to the needle. The needle wall may include a groove for receiving the blade base, which helps keep the needle and blade in the same plane.

BRIEF DESCRIPTION OF THE DRAWINGS

For a more complete understanding of the present invention, and the advantages thereof, reference is now made to the following descriptions taken in conjunction with the accompanying drawings, in which like numbers designate like parts, and in which:

FIG. 1 is a partially broken side elevational view of a surgical apparatus, which shows an embodiment of the invention;

FIG. 2 is a cross-sectional view taken along a line II—II in FIG. 1;

FIG. 8 is an enlarged view of a portion of a needle wall with a groove according to a preferred embodiment of the present invention.

DESCRIPTION OF THE PREFERRED EMBODIMENTS

Figure 3:
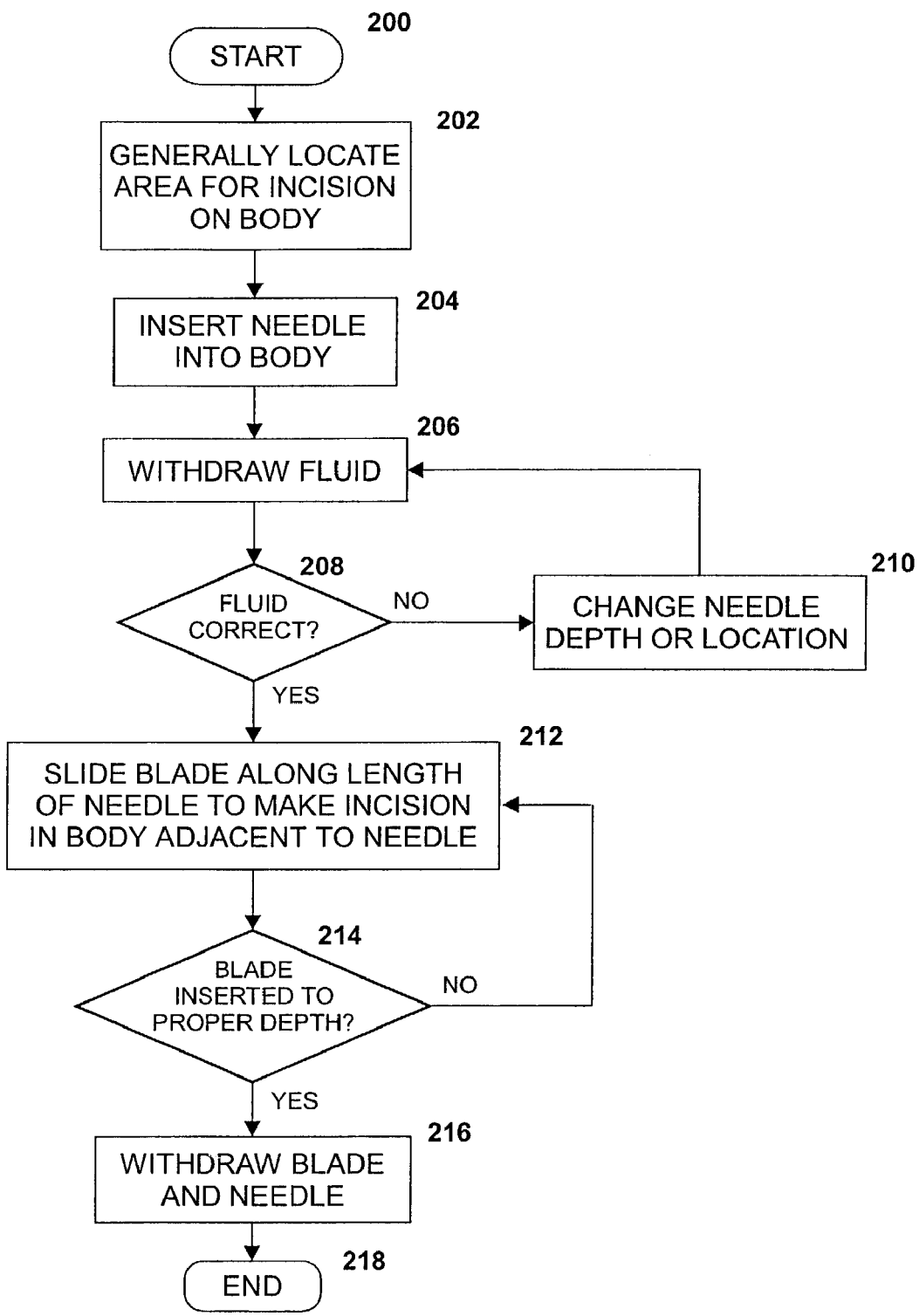
FIG. 3 is a high-level flow chart that illustrates the method and operation of surgically accessing and making an incision in a selected part of a body in accordance with a method of the present invention.

With reference now to the drawings, and in particular with reference to FIG. 1, surgical apparatus 20 includes needle 22 and blades 24 and 36 adjacent to needle 22. Platform 26 slidably engages needle 22, and slides along the length of the needle, and holds blade 24 adjacent to needle 22. Blades 24 and 36 move with platform 26.

The present invention has the advantage of inserting a small probe, i.e., needle 22, into a body to verify a proper location and depth of a proposed incision, so that when the incision is made, it may avoid cutting portions of the body that should not be cut. Evidence of the depth and location may be examined external to the body as fluid (either liquid or gas) is aspirated, viewed, and tested if necessary. By moving adjacent to the needle, the blade or blades are guided to the location of the tip of the needle, where the fluid has been tested.

In the embodiment shown in FIG. 1, surgical apparatus 20 uses needle 22, which has a point or lancet 28, shaft 30, and female leur lock hub 32. Female leur lock hub 32 is adapted to receive syringe leur lock tip 34.

While the preferred embodiment of surgical apparatus 20 shown in FIG. 1 includes two blades, blade 24 and blade 36, some embodiments of the invention may use a single blade. Blades 24 and 36 are triangularly shaped with an edge of the triangle, such as blade bases 38 and 40, respectively, being the base of the triangular shape. Blade bases 38 and 40 are positioned adjacent to needle shaft 30, and in a preferred embodiment, blades 24 and 36 slide in contact with needle wall 42, along the length of needle shaft 30.

Platform 26 preferably surrounds and slidably engages needle 22 for sliding along an axis through the center of needle shaft 30. Needle 22 passes through opening 46 in platform 26. Platform 26 is also coupled to blades 24 and 36, and preferably holds blade bases 38 and 40 in sliding contact with needle wall 42. In a preferred embodiment, platform 26 and blades 24 and 36 slide along needle shaft 30.

Platform 26 may also include handles or stabilizers 50 and 52. Stabilizers 50 and 52 provide a means for user control of platform 26, needle 22, and blades 24 and 36 as the user positions needle 22 and moves the blades down the needle to make an incision. Stabilizers 50 and 52 provide leverage for control of platform 26 and blades 24 and 36. In use, the user's fingers may be placed in stabilizer openings 54 and 56. Other embodiments of stabilizers 50 and 52 may include curved stabilizer arms that wrap comfortably around a finger, or a loop for completely surrounding the user's finger.

In a preferred embodiment, platform 26 and stabilizers 50 and 52 may be molded and integrally formed of the same material. Platform 26 may be made from plastic. Platform 26 is preferably 5.0–6.0 centimeters by 1.5–2.0 centimeters, and about 2 millimeters thick. Stabilizers 50 and 52 are preferably located 2.0–3.0 centimeters apart, with needle 22 located midway between stabilizers 50 and 52. The size and spacing of platform 26 and stabilizers 50 and 52 may vary depending upon the application.

Needle 22 is hollow from lancet 28 to female leur lock hub 34, having needle wall 44 and inner surface 46. Shaft 30 is preferably between 4.0 and 6.0 centimeters long, and preferably has an outside diameter of between 1.7 and 2.5 millimeters. Needle 22 is preferably made of steel.

Blades 24 and 36 are preferably between 2.0 and 3.0 centimeters along blade bases 38 and 40. Blade edges 60 and 62 are preferably between 1.0 and 1.5 centimeters. Blade angles 64 and 66 are preferably between 25 and 30 degrees, measured from needle wall 42 to cutting edges 68 and 70. The dimensions of blades 24 and 36, including angles 64 and 66 and length of cutting edges 68 and 70 are related to the length and depth of the incision. Therefore, blade sizes are selected for the specific operation. For example, if an endotracheal tube will be placed in the incision, the blades are selected to make an incision to the depth of the trachea, and cut an incision that will accommodate the diameter of the tube.

Syringe 80 may be implemented with a syringe Model No. 309604, Manufactured by Becton, Dickinson and Company, located in Franklin Lakes, N.J. USA 07417. Syringe 80 includes plunger 86, which is used to withdraw fluid, either liquid or gas, through needle 22.

With reference now to FIG. 2, there is depicted a cross-sectional view of surgical apparatus 20 taken along line II—II in FIG. 1, and perpendicular to a center axis of needle 22. As shown, blades 24 and 36 are located on opposite sides of needle shaft 30, and blade bases 38 and 40 are in sliding contact with needle wall 42. To further secure blades 24 and 36 in sliding contact with needle wall 42, needle wall 42 may include longitudinal grooves 90 and 92, wherein the grooves are adapted to receive blade bases 38 and 40, respectively. Longitudinal grooves 90 and 92 include groove walls 94, which help maintain blade base 38 and 40 parallel to the needle axis through the center of needle 22. Groove walls are preferably from 0.5–1.0 millimeters apart. A detailed view of groove walls 94 is shown in FIG. 8.

Blades 24 and 36 are preferably made of surgical steel. Blades 24 and 36 may be implemented using blades similar to those manufactured by Becton, Dickinson and Company, located in Franklin Lakes, N.J. USA 07417 and sold under Model No. 371611. Blades 24 and 36 may be from 0.25 to 0.50 millimeters thick, and blade bases 38 and 40 may be tapered to fit longitudinal grooves 90 and 92, as shown in FIG. 8.

Blades 24 and 36 are securely attached to platform 26 by inserting the blades into a slot in platform 26 that provides a snug, friction fit. Blades 24 and 36 may be held in place by adhesives, or by grooves on the blades that snap into grooves located within the slots of the platform.

A process for using surgical apparatus 20 is illustrated generally in the flowchart of FIG. 3. As shown, the process begins at block 200 and thereafter passes to block 202, wherein the user of the surgical apparatus generally locates an area on a body for an incision. In a preferred method of use, surgical apparatus 20 may be used to make an incision to gain emergency access to a blocked airway in a human body. In that application, the area of the body for incision is the cricothyroid membrane, which is located over the trachea on the front side of a human neck above the collar bone.

Figure 4:
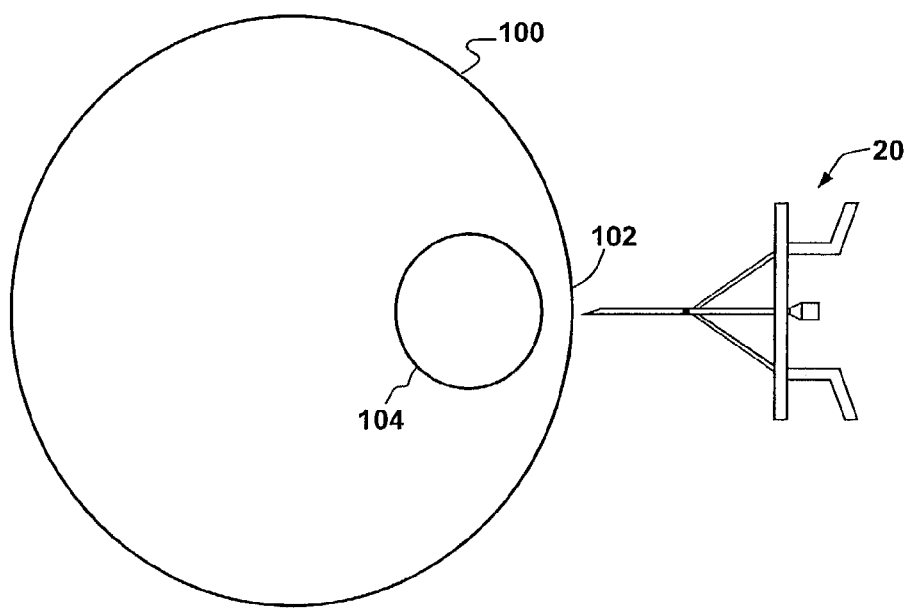
FIGS. 4–7 show a top cross-sectional view of steps in surgically accessing and making an incision in a selected part of a body in accordance with the method of the present invention.

FIG. 4 shows a cross-sectional view of a human neck 100, and surgical apparatus 20 (without a syringe) located near cricothyroid membrane 102. Cricothyroid membrane 102 is on the front of neck 100 and covers trachea 104. In alternative applications of the present invention, the location for an incision may be another part of the body.

Figure 5:
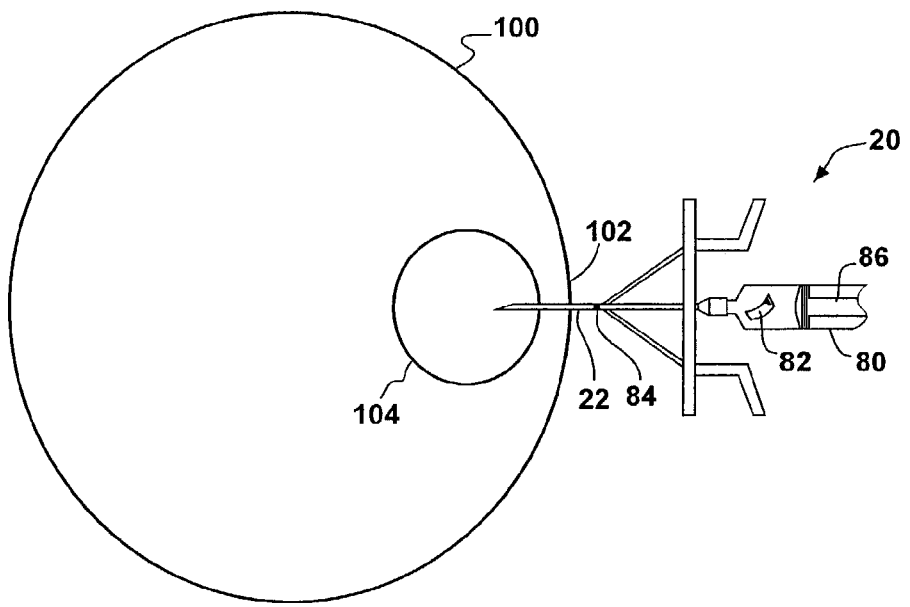

Next, the user inserts the needle into the body at the area for incision, as illustrated in block 204. Continuing with the example above, and referring to FIG. 5, needle 22 is inserted into cricothyroid membrane 102, and has penetrated trachea 104.

Once the needle is inserted to a depth the user believes to be the depth of the needed incision, the user withdraws fluid through needle 22 into syringe 80, as shown at block 206.

Once fluid is withdrawn, the user may examine the fluid and determine whether or not it is the correct fluid for the procedure, as depicted at block 208. Depending upon the procedure being preformed, the user expects a particular type of fluid at the present depth of the needle, and examination of the fluid provides evidence to the user indicating whether or not the needle has been inserted to the proper depth.

For example, if the user intends to make an incision in the trachea, needle 22 is inserted to a depth that should put the tip of the needle within the trachea. A fluid sample is taken while leaving needle 22 in place. As fluid is withdrawn through needle 22, by withdrawing plunger 86 in syringe 80, the user expects to find a gas, such as air or carbon dioxide. If the fluid aspirated is not a gas, and is blood or other liquid, the user may suspect that the needle is not in the appropriate location. It may be too deep or not deep enough, and in either case, the blood may indicate that the trachea has not been properly located.

Thus, in accordance with the present invention, the fluid withdrawn at the depth of penetration of the needle may be liquid or gas, and may be identified, tested, or analyzed visually or by other means. For example, visual analysis through the transparent walls of the syringe body may distinguish blood from pus that may surround an infection.

Visual inspection may also distinguish fluid from gas. Types of gases may be distinguished using a gas detection means, such as indicator paper, or litmus paper 82 (see FIG. 1), which is adapted to change colors in the presence of carbon dioxide. Carbon dioxide detecting litmus paper may be implemented using purple litmus paper sold by Nellcor Puritan-Bennett, Pleasonton, Calif. In the presence of carbon dioxide the paper turns yellow. When performing a cricothyroidotomy, this yellow change produced by carbon dioxide will indicate the needle is properly positioned in the trachea.

If the fluid does not have the correct characteristics according to the procedure being performed, the user may change the needle depth or location, as depicted at block 210. Following this change, the process iteratively returns to block 206, wherein fluid may be once again withdrawn and examined.

Figure 6:
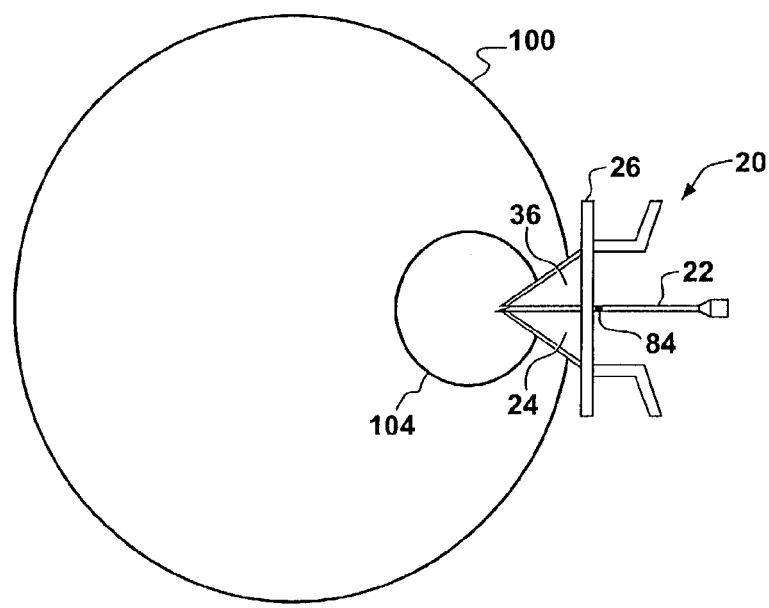

If the correct fluid or contents for the procedure is withdrawn, the process continues to block 212, wherein a blade is moved or slid along the length of the needle to make an incision in the body adjacent to the blade, as illustrated at block 212 and in FIG. 6. As blades 24 and 36 are slid along the length of needle 22, the user continuously determines whether or not the blade has been inserted to the proper depth, as depicted at block 214. If the blade has not been inserted to the proper depth, the user continues to slide the blade to make the incision, as shown at block 212. If the blade has been inserted to the proper depth, the user withdraws the blade and the needle to leave a precise incision to the proper depth, as illustrated at block 216 and FIG. 7.

Figure 7:
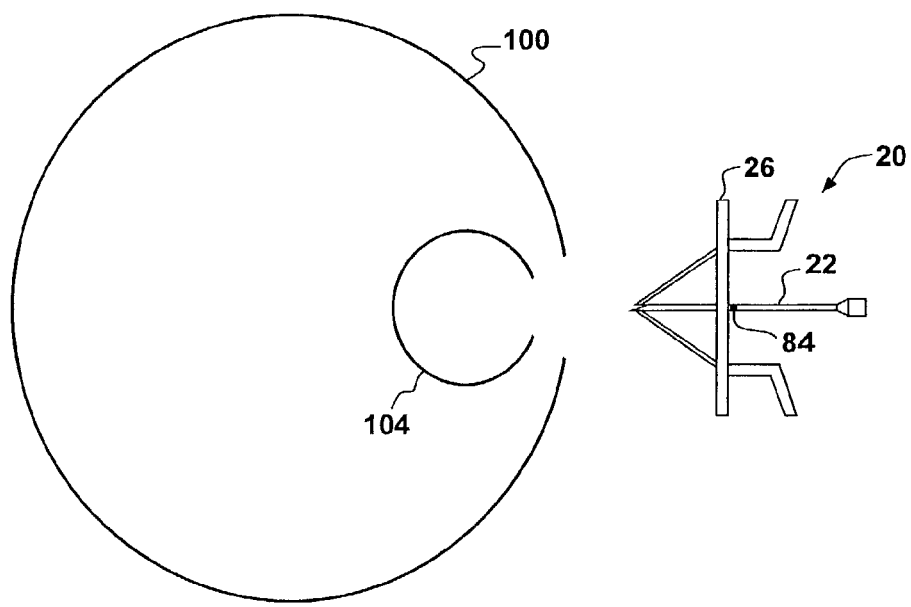

In a preferred embodiment, depth indicator 84 on needle shaft 30 may be used as a reference mark relative to platform 26 to show the depth of blades 24 and 36 as they are moved down needle shaft 30 toward lancet 28. As shown in the embodiment of FIGS. 6 and 7, when blades 24 and 36 extend even with lancet 28, depth indicator 84 appears as it emerges from the hole in platform 26.

As an alternative to withdrawing the blade and needle as shown in block 216 in FIG. 3, only the blade may be withdrawn, and the needle may remain in the incision, or in the cavity, so it can be used as a guide for inserting another tool or instrument, such as hemostats.

The surgical apparatus of the present invention may be used to place a tube or catheter in a body using the Seldinger technique or method. The Seldinger method uses steps 200–210 in FIG. 3 to locate the needle in the trachea, or a blood vessel, or other tubular part of a body that might receive a catheter. Once the needle is properly located, the syringe is removed and a guide wire is threaded through the needle and into the vessel (where "vessel" may be broadly defined as a tube or canal in which a fluid is contained and conveyed). In this application, the needle has an inner diameter large enough to permit the guide wire to pass through the needle.

Once the guide wire is in the vessel, the blades may be slid down the needle to cut the skin at the needle entry site to enlarge the opening for receiving a dilator or catheter sheath, which has a diameter larger than the needle. Blades on a surgical apparatus for this technique are relatively small, and sized for making an incision for the catheter selected for the operation, and for making an incision to the proper depth, through the skin and not the vessel. As an alternative, the blades may be used to enlarge the entry site before the syringe is removed and the guide wire is inserted, which means the syringe can be used to enhance the support and control of the apparatus, making the cutting step easier.

Once the entry site is enlarged, the needle and blade assembly of the present invention is removed along the guide wire, leaving the guide wire in place in the incision. Next, the dilator is threaded over the guide wire and advanced into the skin opening to stretch the tissues. Then the dilator is removed and the catheter sheath is inserted well within the vessel. Finally, the guide wire is removed.

In another application that requires larger or longer incisions, after inserting the blades of the surgical apparatus, the blades may be moved horizontally in the incision, along the surface of the body, where the blade cuts a path as the needle follows, and the platform sets the maximum depth of the blade. Fluid may be aspirated and examined at intervals along the path to determine whether the incision is long enough, or whether the incision has extended into another part of the body.

The foregoing description of a preferred embodiment of the invention has been presented for the purpose of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of surgically accessing and making an incision in a selected part of a body comprising the steps of:
    inserting a needle into part of the body;
    withdrawing fluid from the body through the needle to determine if the needle is located in the selected part of the body; and
    sliding a blade along the length of the needle to make an incision in the body adjacent to the needle.

2. The method of surgically accessing and making an incision in a selected part of a body according to claim 1 wherein the step of withdrawing fluid from the body to determine if the needle is located in the selected part of the body further includes withdrawing a gas from the body to determine if the needle is located in the selected part of the body.

3. The method of surgically accessing and making an incision in a selected part of a body according to claim 1 wherein the step of withdrawing fluid from the body to determine if the needle is located in the selected part of the body further includes withdrawing a liquid from the body to determine if the needle is located in the selected part of the body.

4. The method of surgically accessing and making an incision in a selected part of a body according to claim 2 wherein the step of withdrawing a gas from the body to determine if the needle is located in the selected part of the body further includes withdrawing carbon dioxide from the body to determine if the needle is located in a trachea of a human body.

5. The method of surgically accessing and making an incision in a selected part of a body according to claim 3 wherein the step of withdrawing a liquid from the body to determine if the needle is located in the selected part of the body further includes withdrawing pus from the body to determine if the needle is located in an abscess in a human body.

6. The method of surgically accessing and making an incision in a selected part of a body according to claim 1 wherein the step of sliding a blade along the length of the needle to make an incision in the body adjacent to the needle further includes sliding a triangular blade along the length of the needle to make an incision in the body adjacent to the needle, wherein a cutting edge of the blade is at an angle with respect to a shaft of the needle, and where in a vertex of the angle is toward a point end of the needle.

7. The method of surgically accessing and making an incision in a selected part of a body according to claim 1 wherein the step of sliding a blade along the length of the needle to make an incision in the body adjacent to the needle further includes sliding a blade located in a groove in a needle wall along the length of the needle to make an incision in the body adjacent to the needle.

8. The method of surgically accessing and making an incision in a selected part of a body according to claim 1 wherein the step of sliding a blade along the length of the needle to make an incision in the body adjacent to the needle further includes sliding a blade along the length of the needle until a depth of the blade is the same as the depth of the needle to make an incision in the body adjacent to the needle.

9. The method of surgically accessing and making an incision in a selected part of a body according to claim 1 wherein the step of sliding a blade along the length of the needle to make an incision in the body adjacent to the needle further includes sliding a blade along the length of the needle until a depth of the blade is a selected depth relative to the depth of the needle, to make an incision in the body adjacent to the needle.

10. The method of surgically accessing and making an incision in a selected part of a body according to claim 1 wherein the needle includes a depth indicator, and wherein the step of sliding a blade along the length of the needle to make an incision in the body adjacent to the needle further includes sliding a blade along the length of the needle until the blade reaches a preselected position relative to the depth indicator, to make an incision in the body adjacent to the needle.

11. A surgical apparatus for accessing and making an incision in a selected part of a body comprising:
   a hollow needle, having a needle point and a needle wall that defines a needle tube, the needle for inserting into a selected part of the body and withdrawing fluid;
   a blade having a cutting edge and a blade base adjacent to the cutting edge, the blade base adjacent the needle wall along a portion of a length of the needle for making an incision in the body adjacent to the needle; and
   a platform slidably engaging the needle for sliding along the length of the needle, wherein the platform is coupled to the blade for holding the blade base adjacent to the needle.

12. The surgical apparatus for accessing and making an incision according to claim 11 wherein the blade base is in sliding contact with the needle wall.

13. The surgical apparatus for accessing and making an incision according to claim 11 wherein the needle further includes a longitudinal groove along a portion of the needle wall, and wherein the groove receives the base of the blade.

14. The surgical apparatus for accessing and making an incision according to claim 11 wherein the needle includes a shaft, a lancet at an end of the shaft, and a depth indicator on the shaft for indicating the depth of the cutting edge relative to the lancet.

15. The surgical apparatus for accessing and making an incision according to claim 11 wherein the blade defines a blade plane, and the needle is located in the blade plane.

16. The surgical apparatus for accessing and making an incision according to claim 11 further including a syringe coupled to the needle for withdrawing fluid.

17. The surgical apparatus for accessing and making an incision according to claim 16 further including a fluid indicator in the syringe for indicating the presence of a selected fluid in the syringe.

18. The surgical apparatus for accessing and making an incision according to claim 17 wherein the fluid indicator is litmus paper sensitive to the presence of carbon dioxide.

19. The surgical apparatus for accessing and making an incision according to claim 17 wherein the blade is triangular, and the cutting edge is angled with respect to blade base.

* * * * *